United States Patent
Kim

(10) Patent No.: US 9,636,193 B2
(45) Date of Patent: May 2, 2017

(54) ARTICULATOR

(76) Inventor: Se Hun Kim, Jeonju-si (KR)

( * ) Notice: Subject to any disclaimer, the term of this patent is extended or adjusted under 35 U.S.C. 154(b) by 493 days.

(21) Appl. No.: 14/347,647

(22) PCT Filed: Jul. 24, 2012

(86) PCT No.: PCT/KR2012/005897
§ 371 (c)(1),
(2), (4) Date: Mar. 27, 2014

(87) PCT Pub. No.: WO2013/055021
PCT Pub. Date: Apr. 18, 2013

(65) Prior Publication Data
US 2014/0220504 A1    Aug. 7, 2014

(30) Foreign Application Priority Data

Oct. 14, 2011 (KR) .......................... 10-2011-0104989

(51) Int. Cl.
*A61C 11/02* (2006.01)
*A61C 11/06* (2006.01)
*A61C 11/08* (2006.01)

(52) U.S. Cl.
CPC .............. *A61C 11/02* (2013.01); *A61C 11/06* (2013.01); *A61C 11/08* (2013.01); *A61C 11/087* (2013.01)

(58) Field of Classification Search
CPC ......... A61C 11/02; A61C 11/08; A61C 11/06; A61C 11/087; A61C 11/22; A61C 11/25; A61C 11/27
USPC ...................................... 433/55, 57
See application file for complete search history.

(56) References Cited

U.S. PATENT DOCUMENTS

| | | | |
|---|---|---|---|
| 3,905,112 A | | 9/1975 | Swanson |
| 3,908,271 A | * | 9/1975 | Derda ................... A61C 11/022 433/58 |
| 4,024,640 A | * | 5/1977 | Guichet ............... A61C 11/022 433/57 |
| 4,245,987 A | * | 1/1981 | Bertoldi .............. A61C 11/022 433/61 |
| 4,445,855 A | * | 5/1984 | Hobo ................... A61C 11/022 433/27 |
| 4,758,155 A | * | 7/1988 | Marino ................ A61C 11/022 433/54 |
| 5,431,564 A | * | 7/1995 | Guichet ............... A61C 11/022 433/55 |

(Continued)

FOREIGN PATENT DOCUMENTS

| | | |
|---|---|---|
| KR | 10-0865591 | 10/2008 |
| KR | 10-0976043 | 8/2010 |

(Continued)

OTHER PUBLICATIONS

International Search Report Dated Feb. 13, 2013 From the Korean Intellectual Property Office Re. Application No. PCT/KR2012/005897 and Its Translation Into English.

*Primary Examiner* — Nicholas Lucchesi

(57) ABSTRACT

The present invention relates to an articulator. The articulator may significantly improve the coupling force between a maxillary fixing part and a mandibular fixing part. In addition, since the horizontal turning radius of the maxillary fixing part is easily adjustable according to the size of a mandible model, errors that may occur when the state of occlusion between the mandible model and a maxillary model is checked may be easily prevented.

16 Claims, 19 Drawing Sheets

(56) References Cited

U.S. PATENT DOCUMENTS

| | | | | |
|---|---|---|---|---|
| 5,769,634 A | * | 6/1998 | Choi | A61C 11/027 |
| | | | | 433/34 |
| 2007/0134619 A1 | * | 6/2007 | Lee | A61C 11/00 |
| | | | | 433/57 |
| 2012/0129140 A1 | * | 5/2012 | Wren | G09B 23/283 |
| | | | | 434/263 |
| 2012/0329003 A1 | * | 12/2012 | Lee | A61C 11/02 |
| | | | | 433/54 |

FOREIGN PATENT DOCUMENTS

| | | |
|---|---|---|
| KR | 10-2011-0024924 | 3/2011 |
| WO | WO 2013/055021 | 4/2013 |

\* cited by examiner

ARTICULATOR

CROSS-REFERENCE TO RELATED APPLICATIONS

This application is a National Phase of PCT Patent Application No. PCT/KR2012/005897 having International filing date of Jul. 24, 2012, which claims the benefit of priority of Korean Patent Application No. 10-2011-0104989 filed on Oct. 14, 2011. The contents of the above applications are all incorporated by reference as if fully set forth herein in their entirety.

TECHNICAL FIELD

The present invention relates to an articulator which significantly increases the coupling force between a mandibular fixing part and a maxillary fixing part while allowing the horizontal turning radius of the maxillary fixing part to be more easily adjusted, thereby more easily preventing errors that may occur during the process of checking the state of occlusion between a mandible model and a maxillary model.

BACKGROUND ART

In general, an articulator is a device that measures the state of occlusion of teeth and gums, and is used in the fabrication and testing of dentures, crowns, orthodontic appliances and the like. The articulator mechanically simulates the movement of the mandible, i.e. the lower jaw, after models of teeth acquired from a patient, i.e. a maxillary model and a mandible model (5 in FIG. 1), are attached to the articulator.

The articulator is a device that is mainly used, in particular, for diagnosing diseases that may result from the problem of occlusion and making plans for the treatment of such diseases. The articulator is also used in various fields of dental care, such as implant and straightening.

The conventional articulator uses an approach in which a mandibular fixing part on which the mandible model 5 is mounted and a maxillary fixing part on which the maxillary model is mounted pivot about a shaft in a top-bottom direction. However, the elastic force of a spring, i.e. one of parts which connect the mandibular fixing part and the maxillary fixing part to each other, decreases over time. After a preset amount of time has passed, the coupling force between the mandibular fixing part and the maxillary fixing part is significantly reduced, which is problematic.

In addition, it is impossible to adjust the horizontal turning radius of the maxillary model depending on the arc size ("d" in FIG. 1) of the mandible model 5 which is mounted on the mandibular fixing part. Accordingly, there is a problem in that an error occurs in the process of checking the state of occlusion between the mandible model 5 and the maxillary model.

DISCLOSURE

Technical Problem

The present invention has been made to solve the foregoing problems with the related art, and therefore an aspect of the present invention is to provide an articulator which significantly increases the coupling force between a mandibular fixing part and a maxillary fixing part while allowing the horizontal turning radius of the maxillary fixing part to be more easily adjusted, thereby more easily preventing errors that may occur during the process of checking the state of occlusion between a mandible model and a maxillary model.

Technical Solution

According to an aspect of the present invention, provided is an articulator that includes: a mandibular fixing part, wherein a mandible model is separably fixed to a front upper portion of the mandibular fixing part; a maxillary fixing part, a rear lower portion of the maxillary fixing part being connected to a rear upper portion of the mandibular fixing part via a shaft member wherein a maxillary model is separably fixed to a front lower portion of the maxillary fixing part; and a connecting part including a push switch member, an upper portion of the push switch member being axially coupled to a rear portion of a lower surface of the maxillary fixing part, a front attachment member provided on the push switch member, and a rear attachment member provided on a rear portion of the maxillary fixing part and attached to the front attachment member.

It is preferred that the front attachment member and the rear attachment member be implemented as magnets, the magnet of the front attachment member and the magnet of the rear attachment member having different polarities.

It is preferred that the articulator further include a plurality of support members respectively adjoining to one side and the other side of the shaft member to support the shaft member, one of the plurality of support members being inserted into both sides of the rear lower portion of the maxillary fixing part. The plurality of support members includes: a plurality of first support members inserted into one side of the rear lower portion of the maxillary fixing part, each of the plurality of first support members having an accommodation recess in a central portion, the accommodation recess being opened forward; and a plurality of second support members inserted into the other side of the rear lower portion of the maxillary fixing part, each of the plurality of second support members having an accommodation recess in a central portion, the accommodation recess being opened forward. Each of the plurality of first support members has an inclined surface on one side of an inner circumference of a central portion, the inclined surface being flared and inclined outward, and each of the plurality of second support members has an inclined surface on the other side of an inner circumference of a central portion, the inclined surface being flared and inclined outward. The inclined surfaces of the plurality of first support members have different lengths, and the inclined surface of the plurality of second support members have different lengths.

It is preferred that the articulator further include a fixing part which fixes positions of the plurality of support members which are respectively inserted into the both sides of the rear lower portion of the maxillary fixing part. The fixing part includes: fixing pins which comprise a first fixing pin and a second fixing pin horizontally extending through the both sides of the rear lower portion of the maxillary fixing part and one of the plurality of support members; and rotary members which comprise a first rotary member and a second rotary member, lower portions of the first rotary member and the second rotary member being axially coupled with the both sides of the rear lower portion of the maxillary fixing part, respectively. The first rotary member has an arc-shaped accommodation recess which houses one side of the first fixing pin therein, and the second rotary member has an arc-shaped accommodation recess which houses the other side of the second fixing pin therein.

It is preferred that the articulator further include a replaceable mandible model size-measuring part, a rear lower portion of the mandible model size-measuring part being connected to the rear upper portion of the mandibular fixing part via the shaft member. The mandible model size-measuring part includes measuring indicators formed at preset intervals on an upper surface thereof. The measuring indicators measure a size of the mandible model which is separably fixed to the front upper portion of the mandibular fixing part.

It is preferred that the measuring indicators be implemented as marking lines.

It is preferred that the measuring indicators be embossed on or engraved into the upper surface of the mandible model size-measuring part.

It is preferred that the measuring indicators include a sticker which has marking lines formed on an upper surface thereof.

It is preferred that the articulator further include a support plate disposed on a lower surface of the mandible model size-measuring part. The support plate adjoins to upper surfaces of teeth of the mandible model that is toothed or upper surfaces of the mandible model that is toothless.

It is preferred that the articulator further include a support structure disposed on a lower surface of the mandible model size-measuring part. The mandible model is bisected into a toothed mandible model that is at one side and a toothed mandible model that is at the other side, and the support structure adjoins to upper surfaces of teeth of the toothed mandible model or the toothed mandible model.

Advantageous Effects

According to the present invention, it is possible to significantly increase the coupling force between the mandibular fixing part and the maxillary fixing part using the front attachment member and the rear attachment member which have different polarities while allowing the horizontal turning radius of the maxillary fixing part to be more easily adjusted, thereby more easily preventing errors that may occur during the process of checking the state of occlusion between the mandible model and the maxillary model.

DESCRIPTION OF THE REFERENCE NUMERALS IN THE DRAWINGS

Figure 1:
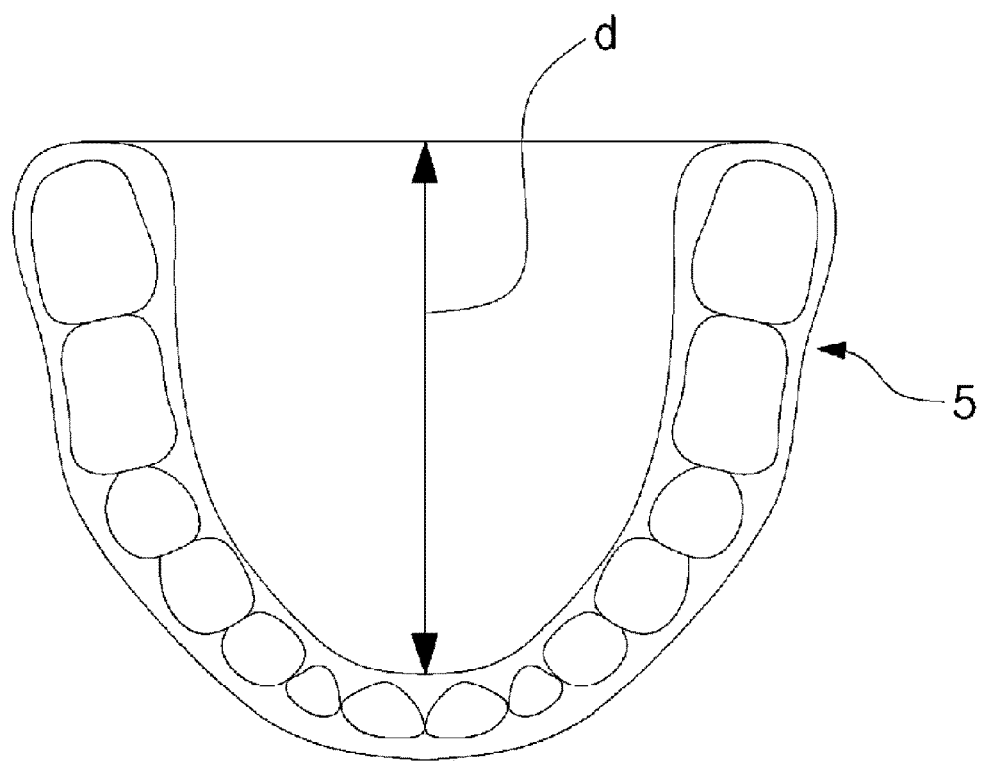
FIG. 1 is a top-plan view schematically showing a mandible model.

10: mandibular fixing part, 20: maxillary fixing part
30: connecting part, 40: adjustment screw
41: forward-backward adjustment screw, 43: lateral adjustment screw
50: fixing part, 60: mandible model measuring-part
70: support plate, 80: support structure
90: magnet, 171, 173, 175, 177: attachment member (magnet)
210: shaft member, 220: insertion recess
230: support member, 260: maxillary fixing part rear lower frame
261: space section, 263: guide recess
265: slot, 270: outer support member
271: insertion recess, 272: guide groove
273: guide member, 274, 275: attachment member fixing recess
280: inner support member, 281: insertion recess
282: guide member, 283: inclined surface
284: attachment fixing recess, 310: push switch member
320: front attachment member, 330: rear attachment member

BEST MODE

Reference will now be made in detail to exemplary embodiments of the present invention in conjunction with the accompanying drawings. It should be understood that the scope of the present invention is not limited to the following embodiments and various modification can be made by a person skilled in the art without departing from the technical concept of the present invention.

Figure 2:
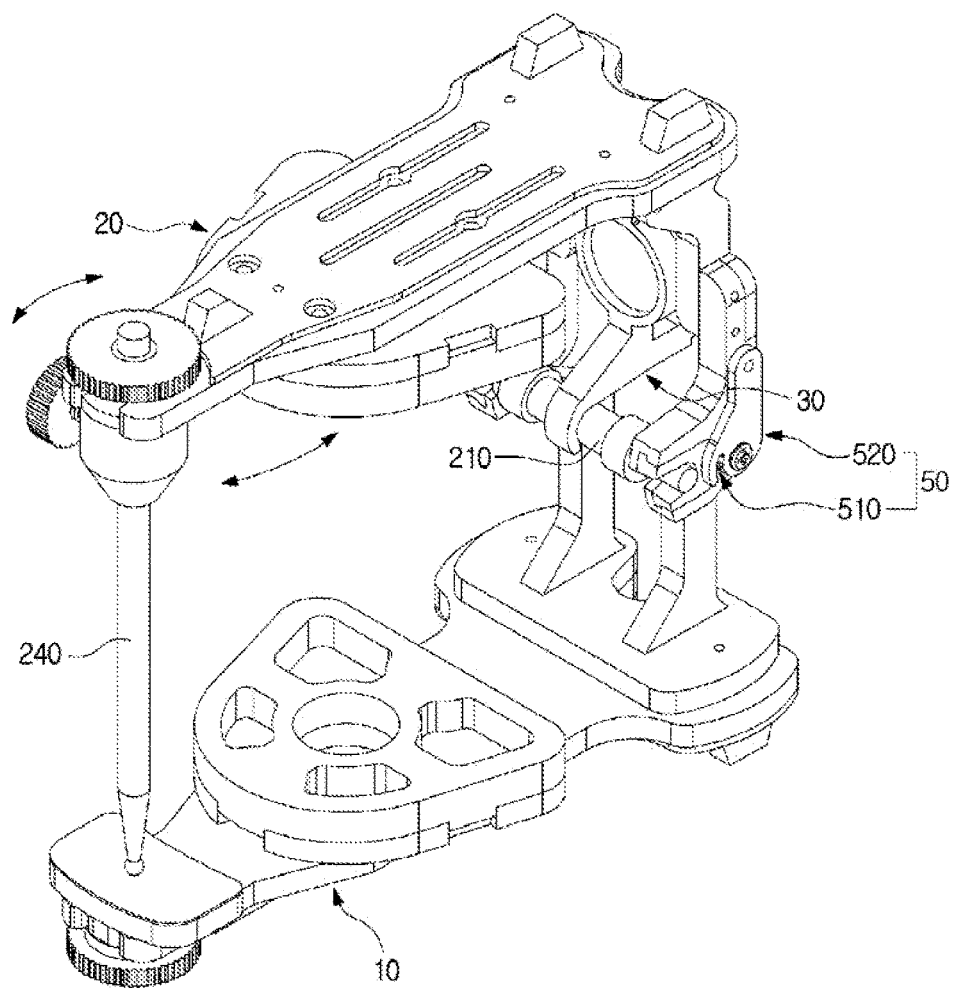
FIG. 2 is a perspective view schematically showing an articulator according to an embodiment of the present invention.
Figure 3:
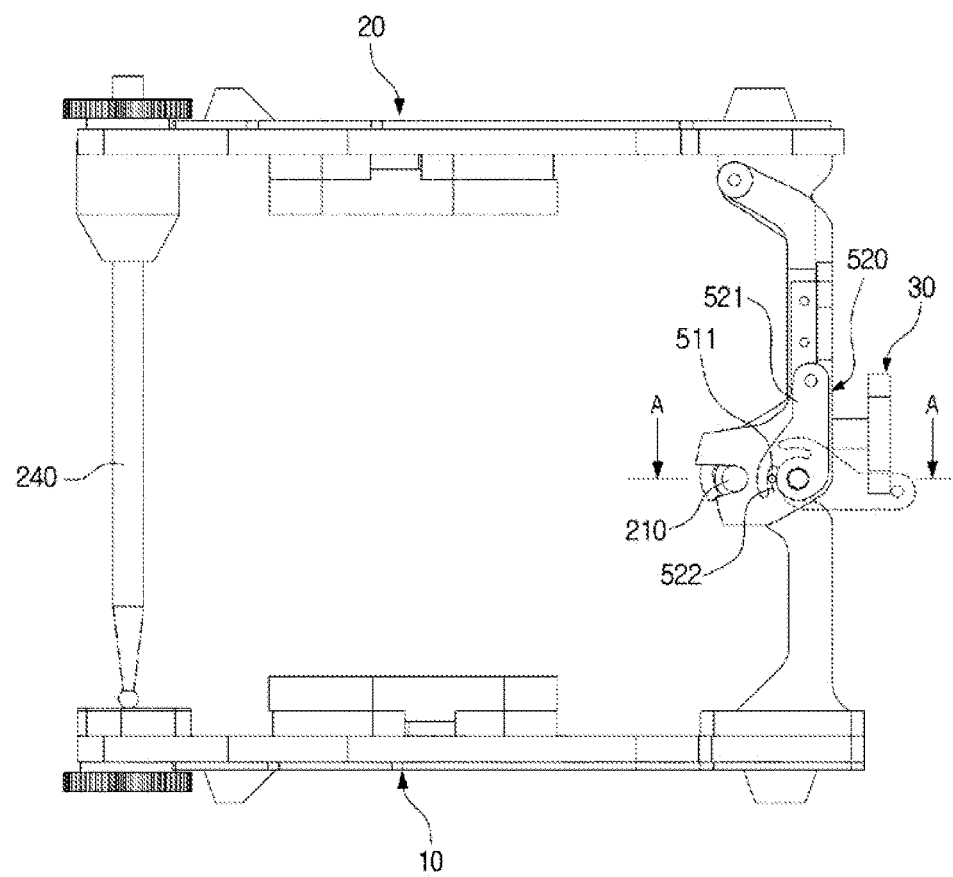
FIG. 3 is a right side-elevation view of FIG. 1.
Figure 4:
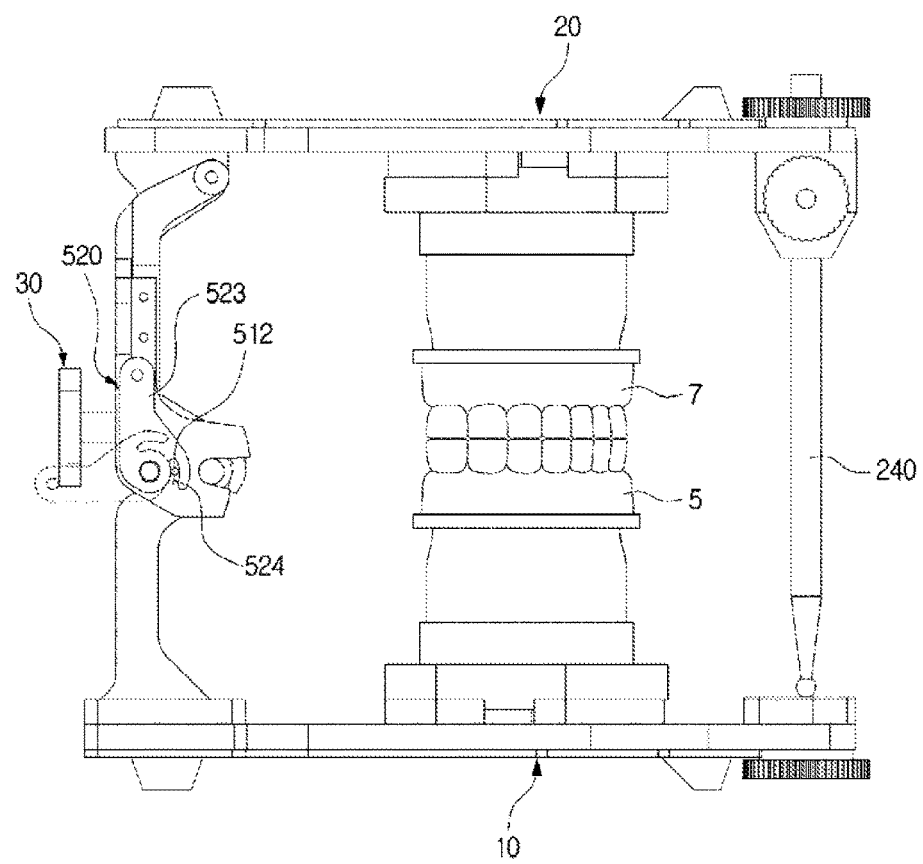
FIG. 4 is a left side-elevation view of FIG. 1.

FIG. 2 is a perspective view schematically showing an articulator according to an embodiment of the present invention, FIG. 3 is a right side-elevation view of FIG. 1, and FIG. 4 is a left side-elevation view of FIG. 1.

As shown in FIG. 2 to FIG. 4, the articulator according to an embodiment of the present invention includes a mandibular fixing part 10, a maxillary fixing part 20 and a connecting part 30.

First, a mandible model 5 is separably fixed to the front upper portion of the mandibular fixing part 10.

In addition, a maxillary model 7 is separably fixed to the front lower portion of the maxillary fixing part 20.

The rear lower portion of the maxillary fixing part 20 can be connected to the rear upper portion of the mandibular fixing part 10 via a shaft member 210 so as to be pivot in the top-bottom direction. Since this is already known and will be apparent to a person skilled in the art to which the present invention relates so that he/she can easily put the present invention into practice, a detailed description thereof will be omitted hereinafter.

A guide pin 240 which maintains the maxillary fixing part 20 and the mandibular fixing part 10 in the horizontal state can be provided on the front portion of the maxillary fixing part 20 such that the guide pin 240 extends vertically and is movable in the top-bottom direction. The guide pin 240 is positioned in front of the maxillary model 7.

Figure 5:
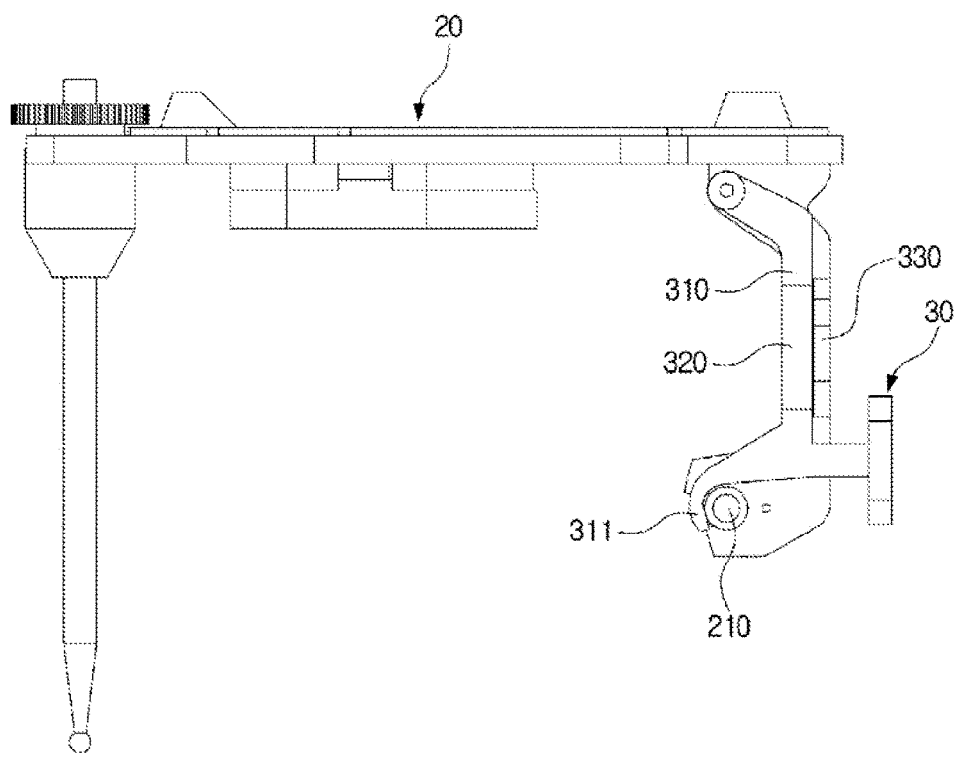
FIG. 5 and FIG. 6 are right side-elevation views schematically showing the maxillary fixing part.
Figure 6:
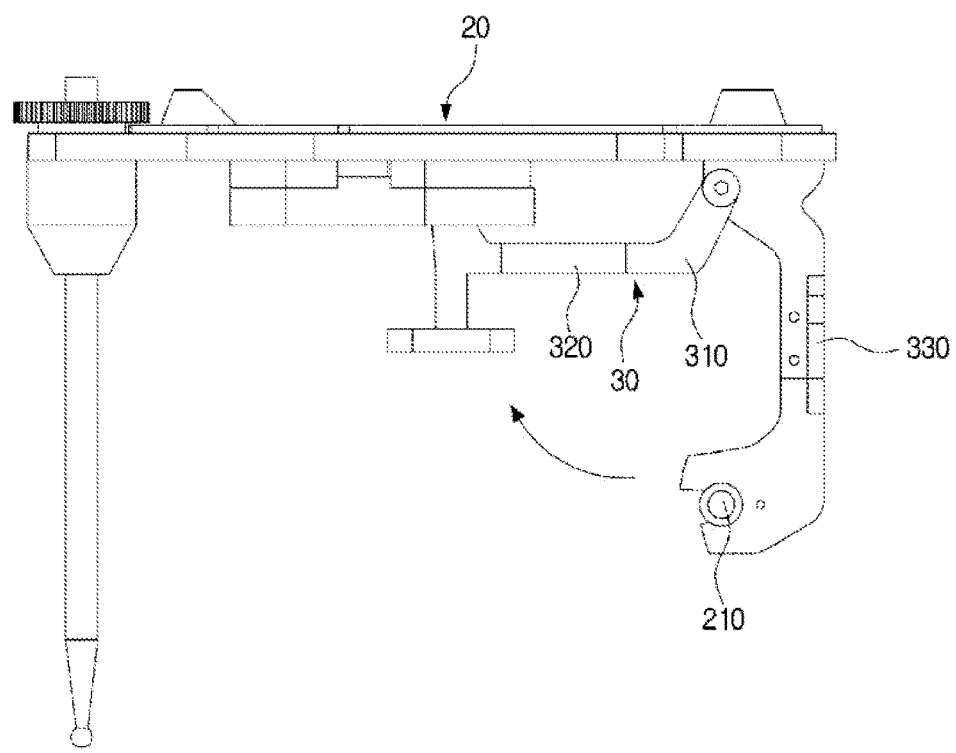

FIG. 5 and FIG. 6 are right side-elevation views schematically showing the maxillary fixing part 20.

As shown in FIG. 5 and FIG. 6, the connecting part 30 includes a push switch member 310, a front attachment member 320 and a rear attachment member 330.

The upper portion of the push switch member 310 can be axially coupled to the rear central portion of the lower surface of the maxillary fixing part 20.

A hook 311 may be formed integrally on the lower front portion of the push switch member 310.

The hook 311 may be curved such that the hook 311 protrudes forward to be convex from the push switch member 310 in a top-to-bottom direction.

The central portion of the shaft member 210 may be accommodated inside the hook 311.

The front attachment member 320 and the rear attachment member 330 may be implemented as magnets having different polarities.

The front attachment member 320 may be provided integrally on the middle portion of the push switch member 310.

The rear attachment member 330 may be provided integrally on the rear lower portion of the maxillary fixing part 20.

When an operator presses the lower rear portion of the push switch member 310 in the forward direction of the push switch member 310 with the palm, the lower portion of the push switch member 310 with respect to the upper portion of the push switch member 310 rotationally moves in the direction toward the lower surface of the maxillary fixing part 20. In this state, the operator can separate the maxillary fixing part 20 from the mandibular fixing part 10.

In the state in which the push switch member 310 has rotationally moved in the direction toward the lower surface of the maxillary fixing part 20, when the operator rotationally moves the lower portion of the push switch member 310 in the direction toward the rear attachment member 330, the distance between the front attachment member 320 and the rear attachment member 330 decreases gradually. In addition, due to the attractive force occurring between the front attachment member 320 and the rear attachment member 330, the front attachment member 320 and the rear attachment member 330 can stay in the contact state.

At the same time, as the central portion of the shaft member 210 is accommodated inside a hook 311 of the push switch member 310, the mandibular fixing part 10 and the maxillary fixing part 20 can be connected more firmly so as to pivot.

Figure 7:
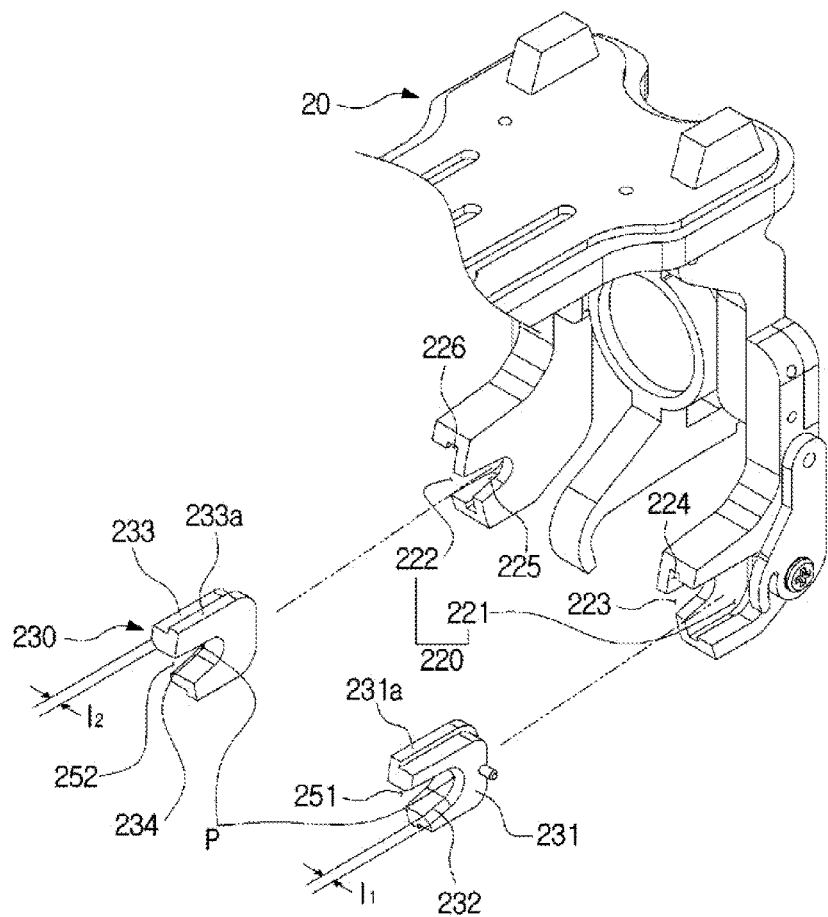
FIG. 7 to FIG. 9 are partial fragmentary perspective views of FIG. 2.
Figure 8:
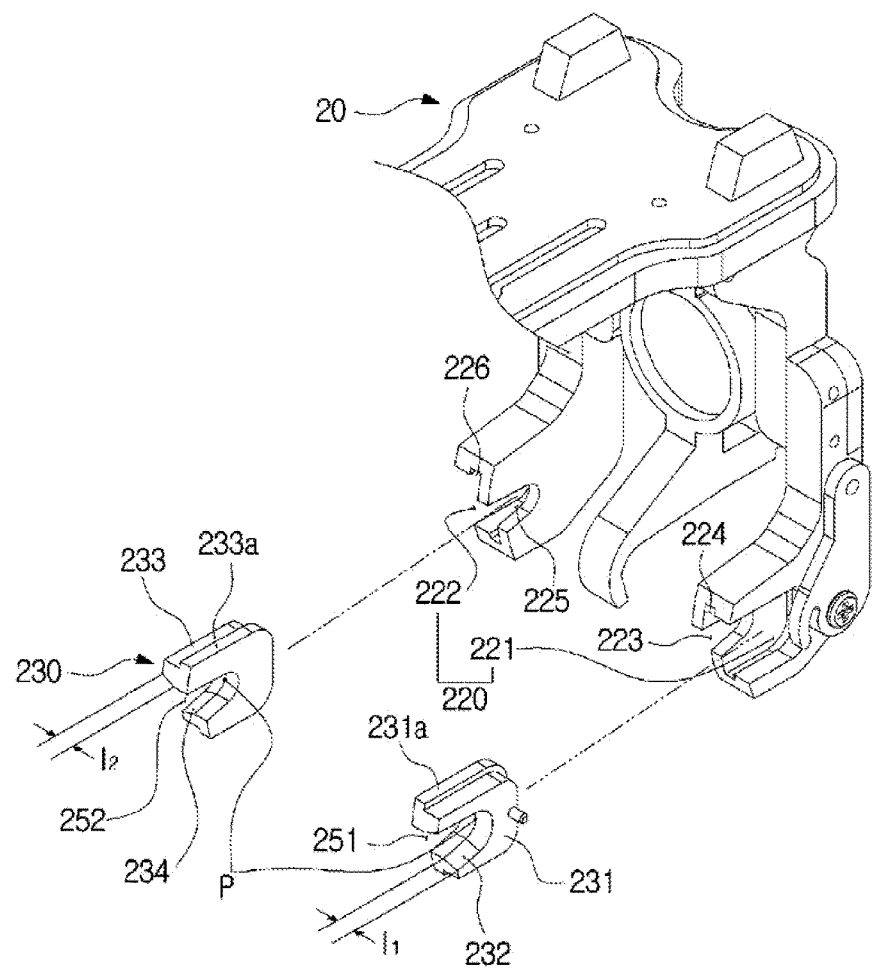
Figure 9:
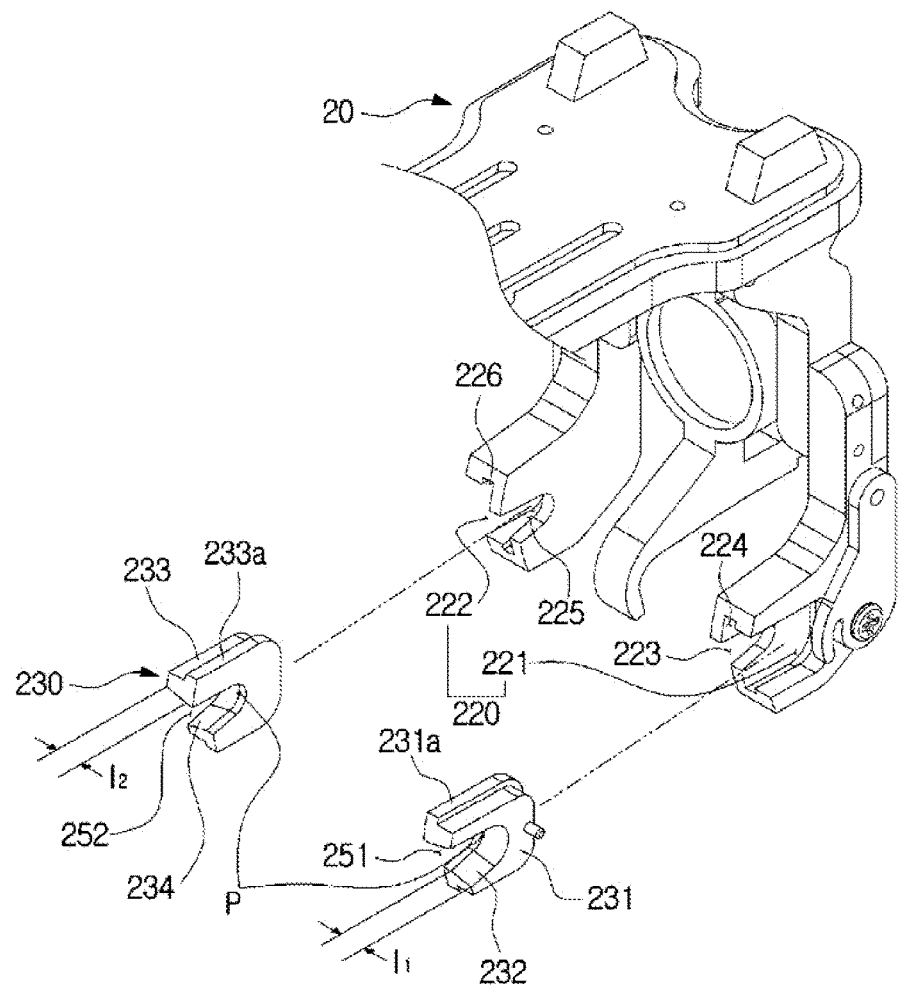

FIG. 7 to FIG. 9 are partial fragmentary perspective views of FIG. 2.

In order to check the state in which the mandible model 5 and the maxillary model 7 occlude each other, the operator rotationally moves the maxillary fixing part 20 by twisting it to the right and left (refer to solid arrows in FIG. 2) so that the state in which the mandible model 5 and the maxillary model 7 occlude each other can be checked.

Here, points of contact P (see FIG. 7 to FIG. 9) where support members 230 which will be described later adjoin to the shaft member 210 may vary in order to easily adjust the horizontal turning radius of the maxillary fixing part 20 depending on the arch size ("d" in FIG. 1) of the mandible model 5.

As the arch size "d" of the mandible model 5 decreases, the points of contact P between the support members 230 and the shaft member 210 are displaced in the direction toward the center of the shaft member 210.

As the arch size "d" of the mandible model 5 increases, the points of contact P between the support members 230 and the shaft member 210 are displaced in the direction toward the opposite ends of the shaft member 210.

More specifically, as shown in FIG. 7, insertion recesses 220 may be formed at both sides of the rear lower portion the maxillary fixing part 20.

The insertion recesses 220 include a first insertion recess 221 which is formed at one side of the rear lower portion of the maxillary fixing part 20 and a second insertion recess 222 which is formed at the other side of the rear lower portion of the maxillary fixing part 20.

The first and second insertion recesses 221 and 222 may be indented to a depth in the direction from the front to the rear of the maxillary fixing part 20 such that the insertion recesses 221 and 222 have a horizontal bottom.

The first insertion recess 221 may be opened forward and at one side.

The first insertion recess 221 may have an accommodation recess 223 in the central portion at the other side. The accommodation recess 223 is indented to a depth in the direction from the front to the rear of the maxillary fixing part 20 such that the accommodation recess 223 has a horizontal bottom and is opened forward.

The first insertion recess 221 may have guide recesses 224 in the upper and lower portions. The guide recesses 224 communicate with the first insertion recess 221. The guide recesses 224 are respectively indented so as to extend a predetermined length from the front to the rear of the maxillary fixing part 20.

The second insertion recess 222 may be opened forward and at the other side.

The second insertion recess 222 may have an accommodation recess 225 in the central portion at one side. The accommodation recess 225 is indented to a depth in the direction from the front to the rear of the maxillary fixing part 20 such that the accommodation recess 225 has a horizontal bottom and is opened forward.

The second insertion recess 222 may have guide recesses 226 in the upper and lower portions. The guide recesses 226 communicate with the second insertion recess 221. The guide recesses 226 are respectively indented so as to extend a predetermined length from the front to the rear of the maxillary fixing part 20.

The above-described support members 230 may be implemented as a plurality of support members 230.

Support members 230 selected from among the plurality of support members 230 are respectively inserted into both the rear lower portions of the maxillary fixing part 20 by the operator. The inserted support members can adjoin to one side and the other side of the shaft member 210 so as to support the shaft member 210.

As shown in FIG. 7 to FIG. 9, the plurality of support members 230 may include a plurality of first support members 231 and a plurality of second support members 233.

A first support member 231 selected from among the plurality of first support members 231 can be inserted in the forward and backward direction into the first insertion recess 221 formed at one side of the rear lower portion of the maxillary fixing part 20.

Each of the plurality of first support members 231 may have an accommodation recess 251 formed in the central portion. The accommodation recess 251 is opened forward, and is indented to a depth in the direction from the front to the rear of the maxillary fixing part 20 so as to have a horizontal bottom.

Each of the first support members 231 may have guide protrusions 231a which protrude vertically from the upper and lower portions. The guide protrusions 231a are respectively fitted into the guide recesses 224.

One second support member 233 selected from among the plurality of second support members 233 can be fitted in the forward and backward direction into the second insertion recess 222 formed at the other side of the rear lower portion of the maxillary fixing part 20.

Each of the plurality of second support members 233 may have an accommodation recess 252 formed in the central portion. The accommodation recess 252 is opened forward, and is indented to a depth in the direction from the front to the rear of the maxillary fixing part 20 so as to have a horizontal bottom.

Each of the first support members 233 may have guide protrusions 233a which protrude vertically from the upper and lower portions. The guide protrusions 233a are respectively fitted into the guide recesses 226.

As shown in FIG. 7 to FIG. 9, each of the plurality of first support members 231 may have an inclined surface 232 formed at one side of the inner circumference of the central portion. The inclined surfaces 232 are flared and inclined in the outward direction of the plurality of first support members 231.

As shown in FIG. 7 to FIG. 9, each of the plurality of second support members 233 may have an inclined surface 234 formed at the other side of the inner circumference of the central portion. The inclined surfaces 234 are flared and inclined in the outward direction of the plurality of second support members 232.

As shown in FIG. 7 to FIG. 9, the inclined surfaces 232 of the plurality of first support members 231 may have different lengths $l_1$.

The inclined surfaces 234 of the plurality of second support members 233 may have different lengths $l_2$.

The points of contact P where the first support members 231 and the second support members 233 adjoin to the shaft member 210 may vary depending on changes in the lengths of the inclined surfaces 232 and 234.

As the length $l_1$ of the inclined surface 232 at one side and the length $l_2$ of the inclined surface 234 at the other side increase, the points of contact P are displaced gradually in the direction toward the center of the shaft member 210.

As the length $l_1$ of the inclined surface 232 at one side and the length $l_2$ of the inclined surface 234 at the other side decrease, the points of contact P are displaced gradually in the direction from the center to one side and the other side of the shaft member 210.

As shown in FIG. 3 and FIG. 4, there may be provided a fixing part 50 which fixes the position of the plurality of support members 230 which are respectively inserted into the both sides of the rear lower portion of the maxillary fixing part 20.

The fixing part 50 may include fixing pins 510 (see FIG. 2) and rotary members 520 (see FIG. 2).

The fixing pins 510 may include a first fixing pin 511 and a second fixing pin 512.

The first fixing pin 511 can extend horizontally through one side of the rear lower portion of the maxillary fixing part 20 and one first support member 231 of the plurality of first support members 231.

The second fixing pin 512 can extend horizontally through the other side of the rear lower portion of the maxillary fixing part 20 and one first support member 231 of the plurality of first support members 231.

The rotary members 520 may include a first rotary member 521 and a second rotary member 523.

As shown in FIG. 3, the lower portion of the first rotary member 521 can be axially coupled with the outer circumference of the lower rear portion of the maxillary fixing part 20.

The first rotary member 521 may have an accommodation recess 522 in the lower front portion. The accommodation recess 522 is convex and in the forward direction of the maxillary fixing part 20, and has the shape of an arc that is opened downward.

The operator can accommodate a portion of the first fixing pin 511 in the accommodation recess 522 or release the portion of the first fixing pin 511 from the accommodated state by rotationally moving the upper portion of the first rotary member 521 upward or downward with respect to the lower portion of the first rotary member 521.

As shown in FIG. 4, the lower portion of the second rotary member 523 can be axially coupled with the outer circumference of the rear lower portion of the maxillary fixing part 20.

The first rotary member 523 may have an accommodation recess 524 in the lower front portion. The accommodation recess 524 is convex and protrudes in the forward direction of the maxillary fixing part 20, and has the shape of an arc that is opened downward.

The operator can accommodate a portion of the second fixing pin 512 in the accommodation recess 524 or release the portion of the second fixing pin 512 from the accommodated state by rotationally moving the upper portion of the second rotary member 523 upward or downward with respect to the lower portion of the second rotary member 523.

In the articulator according to the present invention, it is possible to adjust the position of the shaft member 210 by moving the support member which supports the shaft member 210 using adjustment screws.

The adjustment screws move in a forward and backward direction or a transverse direction. There is an advantage in that the movement of the shaft member 210 can be more precisely adjusted using the adjustment screws than by moving the rotary member that was described in the foregoing embodiment.

In conjunction with the accompanying drawings, reference will now be made to a configuration example in which the shaft member is adjusted with respect to the rear lower frames at a rear side of the maxillary fixing part using the adjustment screws.

Figure 20:
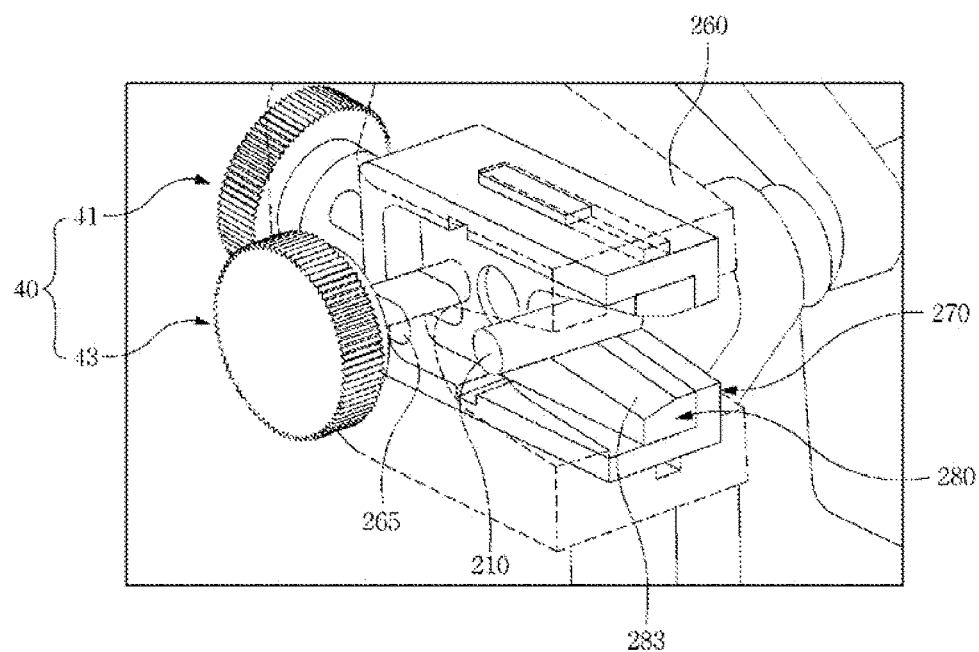
FIG. 20 is a view showing a configuration example in which a shaft member is adjusted with respect to rear lower frames at a rear side of the maxillary fixing part using adjustment screws.

FIG. 20 is a view showing the configuration example in which the shaft member is adjusted with respect to the rear lower frames at the rear side of the maxillary fixing part using the adjustment screws.

Figure 21:
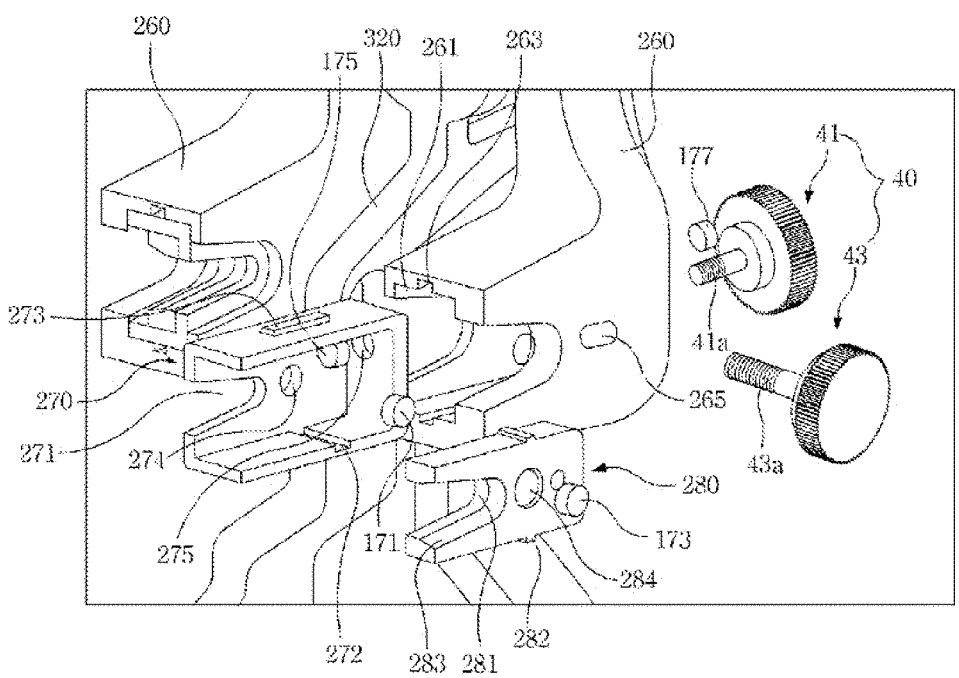
FIG. 21 is a view illustrating a configuration of an outer support member and an inner support member which are disposed on the rear lower frames at the rear side of the maxillary fixing part in FIG. 20.

FIG. 21 is a view illustrating the configuration of an outer support member and an inner support member which are disposed on the rear lower frames at the rear side of the maxillary fixing part in FIG. 20.

Figure 22:
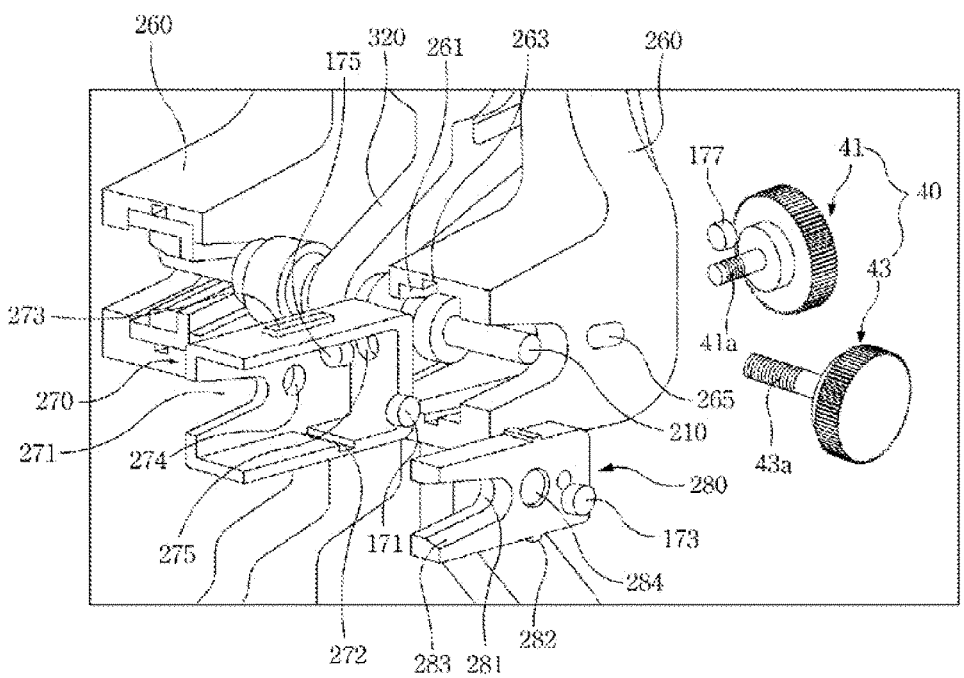
FIG. 22 is a view showing the state in which the shaft member is omitted from the view of FIG. 21.

FIG. 22 is a view showing the state in which the shaft member is omitted from the view of FIG. 21.

In these figures, the outer support member 270 and the inner support member 280 are separately illustrated in the front irrespective of the coupling relationship.

Referring to these figures, the maxillary fixing part 20 according to the present invention has a plurality of rear lower frames 260 on the rear lower portion, the rear lower frames 260 respectively supporting both ends of the shaft member 210.

Each of the plurality of rear lower frames 260 has defined a space section 261 in the lower portion into which a series of configuration members is inserted. Guide recesses 263 are formed on the bottom surface of the upper end and the upper surface of the lower end which are inside the space section 261. Each of the plurality of rear lower frames 260 has slots 265 in both side surfaces, each of the slots 265 being elongated in the forward-backward direction. The lateral adjustment screw 43 is fitted into the corresponding slot 265, and although not shown, each of the plurality of rear lower frames 260 has defined an insertion hole in a rear side into which a forward-backward adjustment screw 41 is fitted.

Each of the plurality of rear lower frames 260 also includes the outer support member 270, the inner support member 280 inserted into the outer support member 270, and a series of attachment members (magnets) 171, 173, 175 and 177 in addition to the adjustment screws 41 and 43.

Each of the plurality of rear lower frames 260 has defined the space section 261 in the lower portion, the space section 261 being opened forward. The outer support member 270 is provided inside the space section 261 so as to support the shaft member 210, and the inner support member 260 is housed inside and coupled to the outer support member 270 so as to move in the longitudinal direction of the shaft member 210.

In addition, the forward-backward adjustment screw 41 is disposed at a rear side of the lower end of each of the rear lower frames 260, and allows the outer support member 270 to move in the forward-backward direction. The lateral adjustment screw 43 is disposed at a side of the lower portion of each of the rear lower frames 260, and allows the inner support member 280 to move in a lateral direction.

Furthermore, the outer support member 270 has defined therein a space section which is opened forward and at one side, and has an insertion recess 271 at a front side in which the shaft member 210 is seated. The outer support member 270 includes guide members 273 on the upper surface and the lower surface. The guide members 273 extend in the forward-backward direction, and guide the sliding of the outer support member 270 into the corresponding space section 261 of the rear lower frames 260. A transverse guide groove 272 is formed on the inner surface, and guides the inner support member 280 to be inserted into the outer support member 270. Attachment member fixing recesses 274 and 275 are formed on the inner surface, and allow the coupled state with the inner support member 280 to be maintained.

The inner support member 280 slides into the outer support member 270, and is coupled with the outer support member 270 in the longitudinal direction in which the shaft member 210 is disposed, i.e. the inner support member 280 moves in a transverse direction.

The inner support member 280 has defined an insertion recess 281 in the front portion in which the shaft member 210 is seated. The inner support member 280 includes transverse guide members 282 on the upper surface and the lower surface. The guide members 282 guide the sliding of the inner support member 280 into the space section of the outer support member 270. The inner support member 280 has a screw hole in a side surface into which the lateral adjustment screw 43 is fitted. The inner support member 280 also has an attachment fixing recess 284 which allows the coupling force between the inner support member 280 and the outer support member 270 to be maintained.

The inner support member 280 has an inclined surface 283 on the front portion. The angle at which the shaft member 210 is inclined varies depending on the inclination of the inclined surface 283.

Since the position of the supporting point of the shaft member 210 during rotation varies depending on the movement of the inner support member 280, the size of the radius of rotation of the shaft member 210 is consequently changed.

The attachment members attached to each of the rear lower frames 260, the outer support member 270 and the inner support member 280 are magnets. Corresponding attachment members have different polarities.

Specifically, constitutional members which have matching magnetic polarities maintain the coupled state at normal times. When the constitutional members are moved away from each other using the adjustment screws 41 and 43, an attractive force acts on the constitutional members. When the adjustment screws 41 and 43 are restored to the original positions, the attractive force causes the two constitutional members that have been spaced apart from each other to return to the original positions.

The slot 265, which is formed at one side of each of the rear lower frame 260 of the maxillary fixing part and into which the lateral adjustment screw 43 is fitted, serves to provide a space where the lateral adjustment screw 43 can also move when the outer support member 270 is moved in the forward-backward direction by the forward-backward adjustment screw 41.

Figure 10:
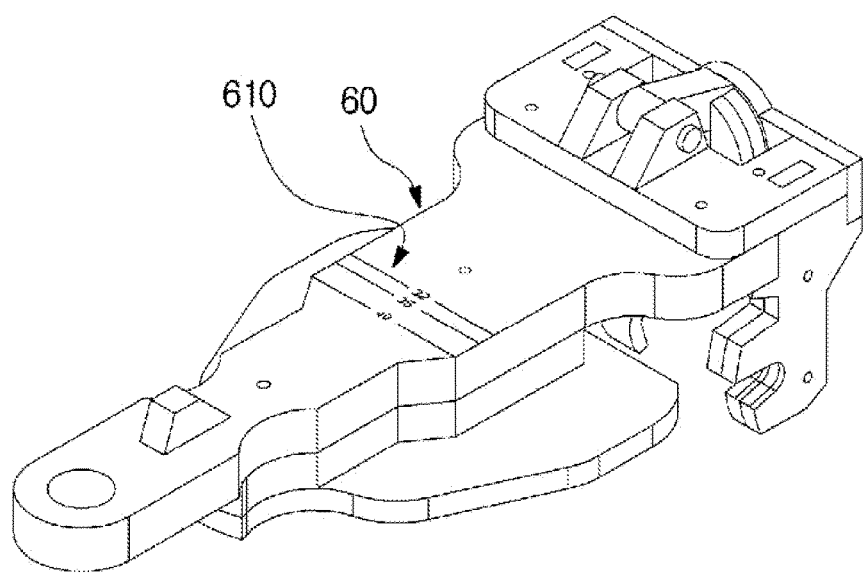
FIG. 10 is a perspective view schematically showing a mandible model size-measuring part.

FIG. 10 is a perspective view schematically showing a mandible model size-measuring part 60.

In addition, the mandible model size-measuring part 60 may be replaceably provided on the rear upper portion of the mandibular fixing part 10 before the maxillary fixing part 20 is connected to the mandibular fixing part 10.

As shown in FIG. 10, the mandible model size-measuring part 60 may have measuring indicators 610 with which the arc size "d" of the mandible model 5 is measured.

The measuring indicators 610 may be implemented with colored marking lines which extend a preset length in a lateral direction. However, the measuring indicators are not limited thereto.

When the measuring indicators 610 are implemented, in particular, as marking lines, the measuring indicators 610 implemented as the marking lines can be painted on a middle portion of the upper surface of the mandible model size-measuring part 60 at regular intervals in the direction from the front to the rear of the mandible model size-measuring part 60.

In order to make it easier for the operator to visually recognize the arc size "d" of the mandible model 5, the mandible model size-measuring part 60 may be made of a transparent synthetic resin or the like. It is also preferred that colored numbers that represent the arc size of the mandible model 5 be marked on the upper surface of the mandible model size-measuring part at positions adjacent to the marking lines.

Like the maxillary fixing part 20, the rear lower portion of the mandible model size-measuring part 60 can be connected to the rear upper portion of the mandibular fixing part 10 so as to pivot in the top-bottom direction along with the shaft member 210.

The operator measures the arc size "d" of the mandible model 5 using the mandible model size-measuring part 60, and then carries out the operation of checking the state of occlusion between the mandible model 5 and the maxillary model 7 by connecting the maxillary fixing part 20 to the mandibular fixing part 10 in place of the mandible model size-measuring part 60.

In addition, the colored numbers can be embossed on or engraved into the upper surface of the mandible model size-measuring part 60 together with the measuring indicators 610 that can be implemented as colored marking lines or the like.

However, although not shown in the figures, it is preferred that the measuring indicators 610 be implemented as a sticker made of a transparent material, with colored marking lines or colored numbers being printed at preset intervals on the upper surface of the sticker.

The sticker with the colored marking lines or colored numbers printed at preset intervals on the upper surface thereof can be attached to the upper surface of the mandible model size-measuring part 60, thereby more simply forming the measuring part 610 on the upper surface of the mandible model size-measuring part 60.

Figure 11:
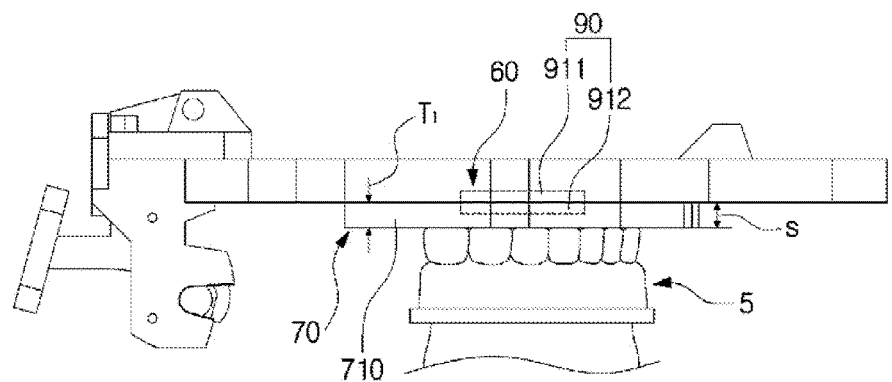
FIG. 11 to FIG. 13 are left side-elevation views schematically showing the state in which a support plate is provided on the lower surface of the mandible model size-measuring part.
Figure 12:
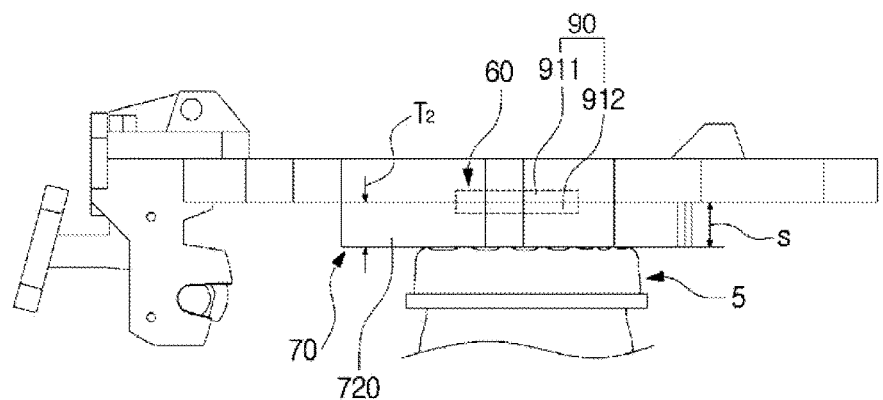
Figure 13:
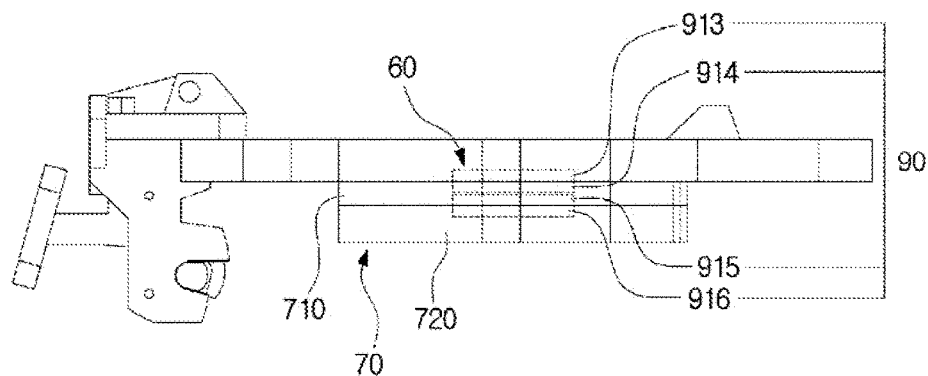

FIG. 11 to FIG. 13 are left side-elevation views schematically showing the state in which a support plate 70 is provided on the lower surface of the mandible model size-measuring part 60.

While the mandible model size-measuring part 60 is configured the same as the maxillary fixing part 20, the support plate 70 may be provided horizontally on the central portion of the lower surface of the mandible model size-measuring part 60, as shown in FIG. 11 to FIG. 13.

A space "s" can be formed between the upper portion of the mandible model 5 and the lower portion of the mandible model size-measuring part 60 depending on the top-bottom width of the mandible model 5 which is fixed to the front upper portion of the mandibular fixing part 10.

The support plate 70 can be positioned in the space "s."

As shown in FIG. 11, the support plate 70 can be implemented as a first support plate 710 which adjoins to the upper surface of teeth which are provided on the upper surface of the mandible model 5 that has teeth.

Alternatively, as shown in FIG. 12, the support plate can be implemented as a second support plate 720 which adjoins to the upper surface of the mandible model 5 that is toothless, i.e. there are no teeth on the mandible model 5.

The top-bottom thickness $T_2$ of the second support plate 320 can be greater than the top-bottom thickness $T_1$ of the first support plate 710 such that the second support plate 720 can more easily adjoin to the upper surface of the toothless mandible model 5.

Due to the support plate 70 positioned in the space "s," the mandible model 5 that is toothed or toothless can more easily stay parallel with the mandible model size-measuring part 60 in a horizontal position. Consequently, the operator can more easily measure the arc size "d" of the toothed or toothless mandible model 5.

As shown in FIG. 13, both the first support plate 710 and the second support plate 720 can be provided horizontally on the middle portion of the lower surface of the mandible model size-measuring part 60.

In addition, the support plate 70 can be fixedly attached in a simple manner via attachment members that can be implemented as magnets 90.

The magnets 90 can include an upper magnet 911 and a lower magnet 912, as shown in FIG. 11 and FIG. 12, or a first magnet 913, a second magnet 914, a third magnet 915 and a fourth magnet 916, as shown in FIG. 13.

The upper magnet 911 and the lower magnet 912 can have different polarities.

The upper magnet 911 can be provided inside the lower central portion of the mandible model size-measuring part 60.

The lower magnet 912 can be provided inside the upper central portion of the first support plate 710 of the support plate 70 or inside the upper central portion of the second support plate 720 of the support plate 70.

The first magnet 913 and the second magnet 914 can have different polarities.

The third magnet 915 and the sixth magnet 916 can have different polarities.

The first magnet 913 can be provided inside the lower central portion of the mandible model size-measuring part 60.

The second magnet 914 can be provided inside the lower central portion of the first support plate 710 of the support plate 70.

The third magnet 915 can be provided inside the lower central portion of the first support plate 710 of the support plate 70.

The fourth magnet 916 can be provided inside the upper central portion of the second support plate 720 of the support plate 70.

Figure 14:
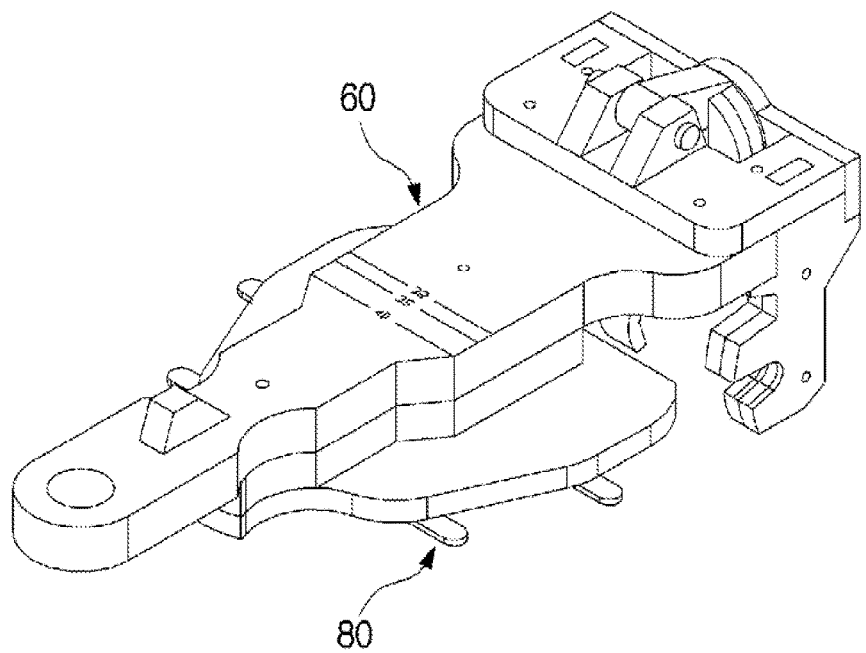
FIG. 14 is a perspective view schematically showing the state in which a support structure is provided on the lower surface of the mandible model size-measuring part.
Figure 15:
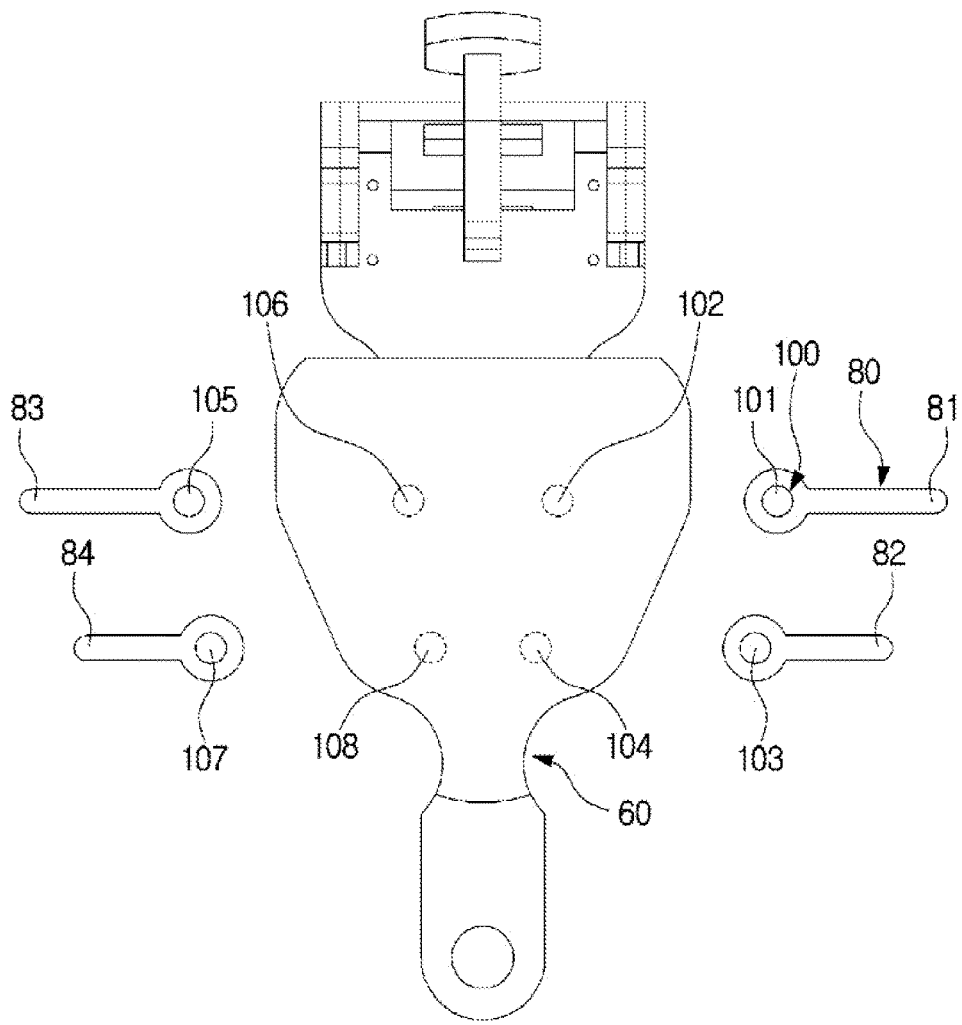
FIG. 15 is a bottom view of FIG. 14.

FIG. 14 is a perspective view schematically showing the state in which a support structure 80 is provided on the lower surface of the mandible model size-measuring part 60, and FIG. 15 is a bottom view of FIG. 14.

As shown in FIG. 14 and FIG. 15, the support structure 80 may be provided on the lower surface of the mandible model size-measuring part 60 in place of the support plate 70.

The mandible model 5 can be bisected into a toothed mandible model (51 in FIG. 16) at one side and a toothed mandible model (52 in FIG. 17) at the other side.

When the toothed mandible model 51 that is at one side is fixed to the front upper portion of the mandibular fixing part 10, the support structure 80 can be provided on the central portion of the lower surface of the mandible model size-measuring part 60.

As shown in FIG. 15, the support structure 80 can include a first support 81 and a second support 82.

The other side of the first support 81 can be axially coupled with one side of the central portion of the lower surface of the mandible model size-measuring part 60.

In the state in which the second support 82 is positioned in front of the first support 81, the other side of the second support 82 can be axially coupled with one side of the central portion of the lower surface of the mandible model size-measuring part 60.

Alternatively, the other side of the first support 81 and the other side of the second support 82 can be fixedly attached in a simple manner to one side of the lower surface of the mandible model size-measuring part 60 via attachment members that can be respectively implemented as magnets 100.

The magnets 100 can include a first magnet 101, a second magnet 102, a third magnet 103 and a fourth magnet 104.

The first magnet 101 and the second magnet 102 have different polarities, and the third magnet 103 and the fourth magnet 104 also have different polarities.

The first magnet 101 can be provided inside the other side of the first support 81.

The second magnet 102 can be provided inside one side of the lower surface of the mandible model size-measuring part 60.

The third magnet 103 can be provided inside the other side of the second support 82.

The fourth magnet 104 can be provided inside one side of the lower surface of the mandible model size-measuring part 60 while being positioned in front of the second magnet 102.

The operator can relocate one side of the first support and one side of the second support 82 by rotationally moving them in the forward-backward direction with respect to the other side of the first support 81 and the other side of the second support 82.

When the toothed mandible model 52 that is at the other side is fixed to the other side of the front upper portion of the mandibular fixing part 10, the support structure 80 can be provided on the other side of the lower surface of the mandible model size-measuring part 60, as shown in FIG. 15.

The support structure 80 can include a third support 83 and a fourth support 84.

One side of the third support 83 can be axially coupled with the other side of the lower surface of the mandible model size-measuring part 60.

In the state in which the fourth support 84 is positioned in front of the third support 83, one side of the fourth support 84 can be axially coupled with the other side of the lower surface of the mandible model size-measuring part 60.

Alternatively, one side of the third support 83 and one side of the fourth support 84 can be fixedly attached in a simple manner to the other side of the lower surface of the mandible model size-measuring part 60 via the attachment members that can be respective implemented as the magnets 100.

The magnet 100 can include a fifth magnet 105, a sixth magnet 106, a seventh magnet 107 and an eighth magnet 108.

The fifth magnet 105 and the sixth magnet 106 have different polarities, and the seventh magnet 107 and the eighth magnet 108 have different polarities.

The fifth magnet 105 can be provided inside one side of the third support 83.

The sixth magnet 106 can be provided inside the other side of the lower surface of the mandible model size-measuring part 60.

The seventh magnet 107 can be provided inside one side of the fourth support 84.

The eighth magnet 108 can be provided inside the other side of the lower surface of the mandible model size-measuring part 60 while being positioned in front of the sixth magnet 106.

The operator can relocate the other side of the third support 83 and one side of the fourth support 84 by rotationally moving them in the forward-backward direction with respect to the other side of the third support 83 and one side of the fourth support 84.

The mandible model 5 that is not bisected, including the toothed mandible model 51 that is at one side and the toothed mandible model 52 that is provided at the other side of the one-side mandible model 51, can be fixed to the other side of the front upper portion of the mandibular fixing part 10.

In this case, as shown in FIG. 15, the support structure 80 including the first to fourth supports 81, 82, 83 and 84 can be provided on both one side and the outer side of the lower surface of the mandible model size-measuring part 60 via the attachment members implemented as the magnets 100 including the first to eighth magnets 101, 102, 103, 104, 105, 106, 107 and 108.

FIG. 16 to FIG. 19 are top-plan views schematically showing the states in which the support structure 80 adjoins to the mandible model 5.

Figure 16:
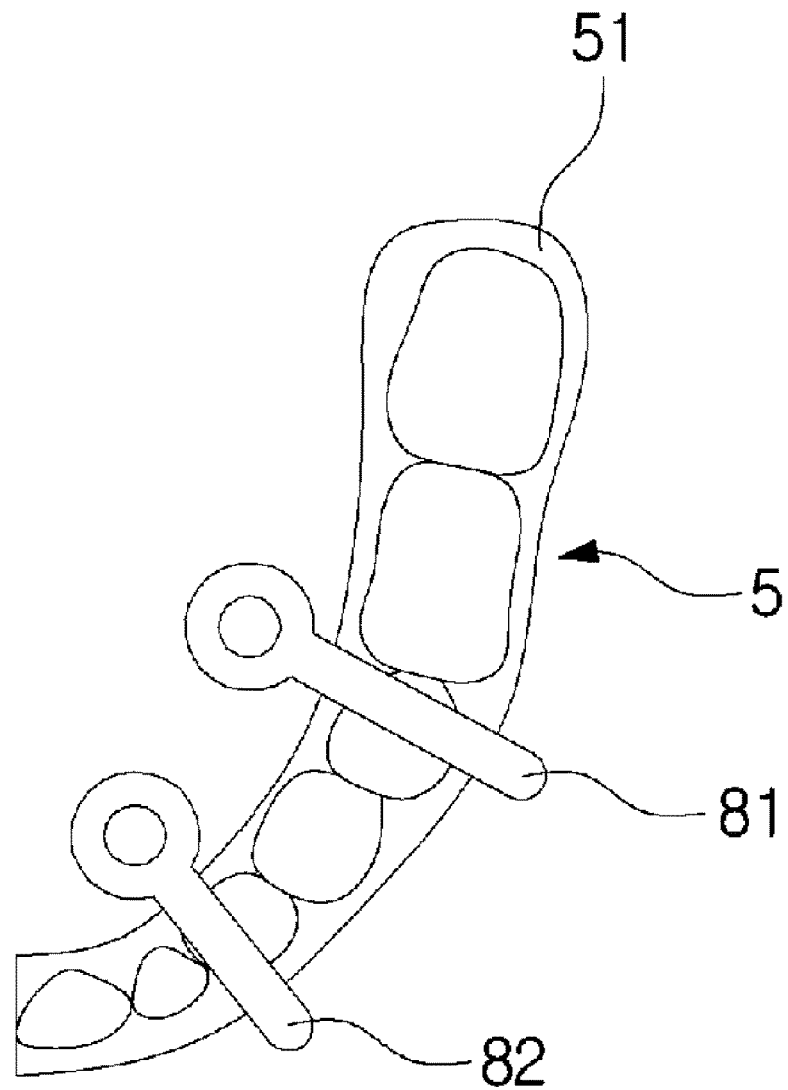
FIG. 16 to FIG. 19 are top-plan views schematically showing the states in which the support structure adjoins to the mandible model that is bisected.

As shown in FIG. 16, the lower surface of the first support 81 and the lower surface of the second support 82 can adjoin to teeth provided on the upper portion of the toothed mandible model 51 that is at one side.

Figure 17:
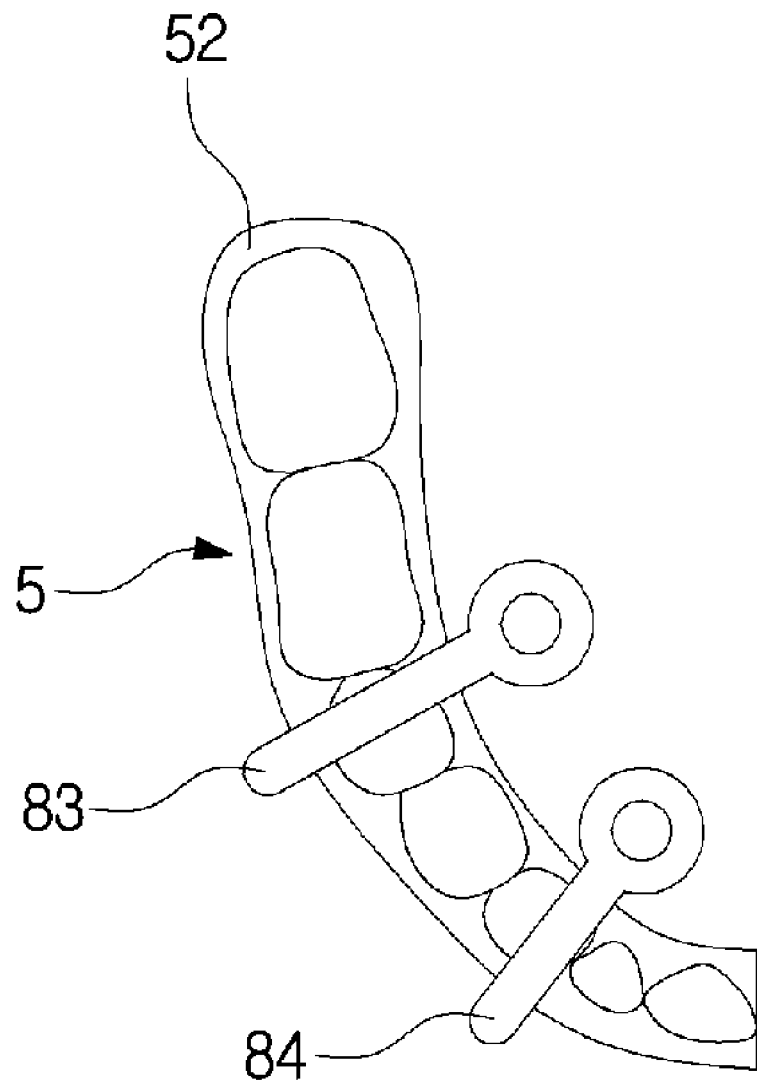

As shown in FIG. 17, the lower surface of the third support 83 and the lower surface of the fourth support 83 can adjoin to the teeth provided on the upper portion of the toothed mandible model 52 that is at the other side.

Figure 18:
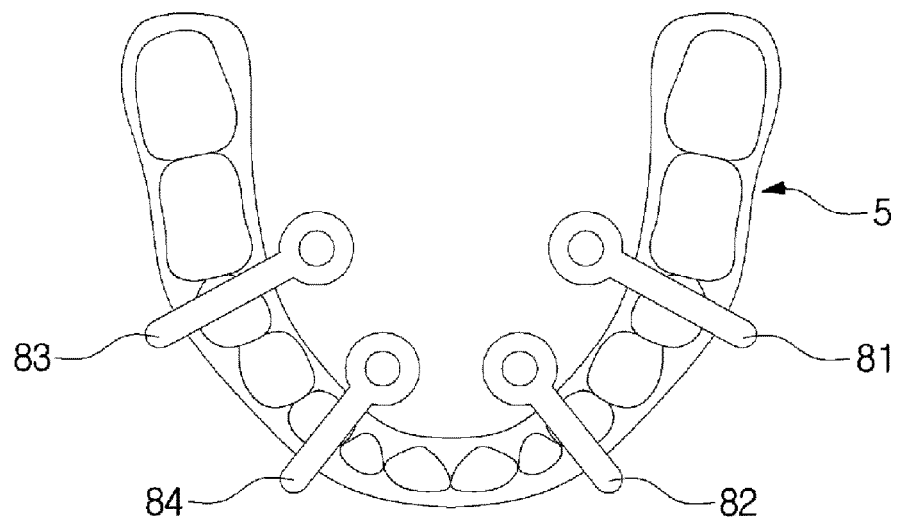

As shown in FIG. 18, the lower surface of the first support 81, the lower surface of the second support 82, the lower surface of the third support 83 and the lower surface of the fourth support 84 can adjoin to teeth provided on the upper portion of the toothed mandible model 5 that is not bisected.

Figure 19:
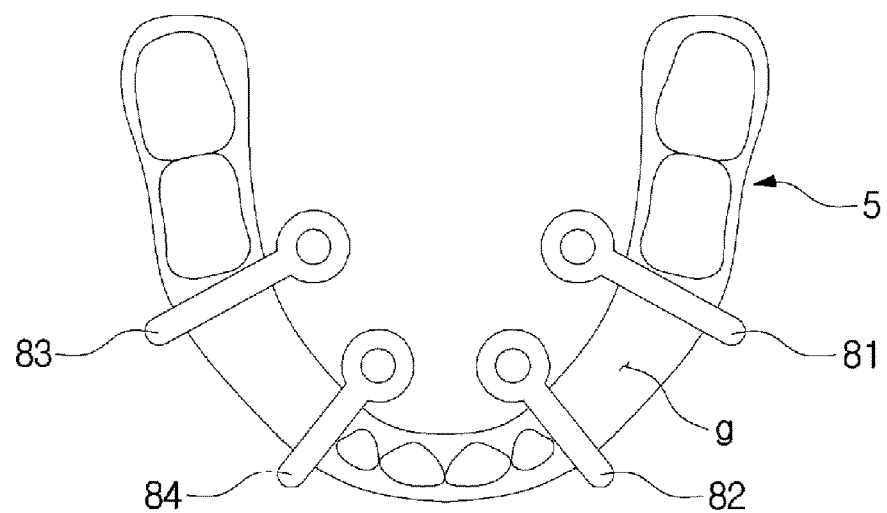

As shown in FIG. 19, spaces "g" may be formed between teeth which are provided on the upper portion of the toothed mandible model 5 that is not bisected. The bottom surface of the space "g" can adjoin to one or all of the lower surface of the first support 81, the lower surface of the second support 82, the lower surface of the third support 83 and the lower surface of the fourth support 84.

Alternatively, although not shown in the figures, surplus plaster may be formed on and protrude upward from front and rear sides of the upper surface of the mandible model 5 that is toothless during the molding process of the toothless mandible model 5.

Such a space "g" can also be formed between lumps of surplus plaster. The bottom surface of the space "g" formed between the lumps of surplus plaster can adjoin to one or all of the lower surface of the first support 81, the lower surface of the second support 82, the lower surface of the third support 83 and the lower surface of the fourth support 84.

According to the present invention as set forth above, it is possible to significantly increase the coupling force between the mandibular fixing part 10 and the maxillary fixing part 20 using the front attachment member 320 and the rear attachment member 330 which have different polarities while allowing the horizontal turning radius of the maxillary fixing part 20 to be more easily adjusted, thereby more easily preventing errors that may occur during the process of checking the state of occlusion between the mandible model 5 and the maxillary model 7.

The invention claimed is:

1. An articulator comprising:
   a mandibular fixing part, wherein a mandible model is separably fixed to a front upper portion of the mandibular fixing part;
   a maxillary fixing part, a rear lower portion of the maxillary fixing part being connected to a rear upper portion of the mandibular fixing part via a shaft member, wherein a maxillary model is separably fixed to a front lower portion of the maxillary fixing part; and
   a connecting part comprising a push switch member, an upper portion of the push switch member being axially coupled to a rear portion of a lower surface of the maxillary fixing part, a front attachment member provided on the push switch member, and a rear attachment member provided on a rear portion of the maxillary fixing part and attached to the front attachment member.

2. The articulator according to claim 1, wherein the front attachment member and the rear attachment member comprise magnets, the magnet of the front attachment member and the magnet of the rear attachment member having different polarities.

3. The articulator according to claim 1, further comprising a plurality of support members respectively adjoining to one side and the other side of the shaft member to support the shaft member, one of the plurality of support members being inserted into both sides of the rear lower portion of the maxillary fixing part, wherein the plurality of support members comprises:
 a plurality of first support members inserted into one side of the rear lower portion of the maxillary fixing part, each of the plurality of first support members having an accommodation recess in a central portion, the accommodation recess being opened forward; and
 a plurality of second support members inserted into the other side of the rear lower portion of the maxillary fixing part, each of the plurality of second support members having an accommodation recess in a central portion, the accommodation recess being opened forward,
 wherein each of the plurality of first support members has an inclined surface on one side of an inner circumference of a central portion, the inclined surface being flared and inclined outward, and each of the plurality of second support members has an inclined surface on the other side of an inner circumference of a central portion, the inclined surface being flared and inclined outward, and
 wherein the inclined surfaces of the plurality of first support members have different lengths, and the inclined surfaces of the plurality of second support members have different lengths.

4. The articulator according to claim 3, further comprising a fixing part which fixes positions of the plurality of support members which are respectively inserted into the both sides of the rear lower portion of the maxillary fixing part, wherein the fixing part comprises:
 fixing pins which comprise a first fixing pin and a second fixing pin horizontally extending through the both sides of the rear lower portion of the maxillary fixing part and one of the plurality of support members; and
 rotary members which comprise a first rotary member and a second rotary member, lower portions of the first rotary member and the second rotary member being axially coupled with the both sides of the rear lower portion of the maxillary fixing part, respectively, wherein the first rotary member has an arc-shaped accommodation recess which houses one side of the first fixing pin therein, and the second rotary member has an arc-shaped accommodation recess which houses the other side of the second fixing pin therein.

5. The articulator according to claim 1, further comprising a replaceable mandible model size-measuring part, a rear lower portion of the mandible model size-measuring part being connected to the rear upper portion of the mandibular fixing part via the shaft member, wherein the mandible model size-measuring part comprises measuring indicators formed at preset intervals on an upper surface thereof, wherein the measuring indicators measure a size of the mandible model which is separably fixed to the front upper portion of the mandibular fixing part.

6. The articulator according to claim 5, wherein the measuring indicators comprise marking lines.

7. The articulator according to claim 6, wherein the measuring indicators are embossed on or engraved into the upper surface of the mandible model size-measuring part.

8. The articulator according to claim 5, wherein the measuring indicators comprises a sticker which has marking lines formed on an upper surface thereof.

9. The articulator according to claim 5, further comprising a support plate disposed on a lower surface of the mandible model size-measuring part, wherein the support plate adjoins to upper surfaces of teeth of the mandible model.

10. The articulator according to claim 5, further comprising a support structure disposed on a lower surface of the mandible model size-measuring part, wherein the mandible model is bisected into a toothed mandible model that is at one side and a toothed mandible model that is at another side, and the support structure adjoins to the toothed mandible model.

11. The articulator according to claim 1,
 wherein the maxillary fixing part comprises:
 a plurality of rear lower frames disposed on the rear lower portion, the plurality of rear lower frames respectively supporting both ends of the shaft member, each of the plurality of rear lower frames having a space section in a lower portion, the space section being opened forward;
 an outer support member disposed inside the space section, wherein the outer support member moves a position of the shaft member in a forward-backward direction; and
 an inner support member housed inside and coupled with the outer support member, wherein the inner support member moves in a longitudinal direction of the shaft member, and
 wherein a forward-backward adjustment screw which moves the outer support member in the forward-backward direction is disposed at a rear side of a lower portion of each of the plurality of rear lower frames, and a lateral adjustment screw which moves the inner support member in a lateral direction is disposed at a side of the lower portion of each of the plurality of rear lower frames.

12. The articulator according to claim 11, wherein the outer support member has an inner space which is opened forward and at one side, the outer support member comprising:
 an insertion recess formed at a front side in which the shaft member is seated;
 guide members respectively extending in a forward-backward direction on upper and lower surfaces so as to guide sliding into the space sections of the plurality of rear lower frames; and
 magnet fixing recesses (274, 275) which maintain a coupled state with the inner support member.

13. The articulator according to claim 12, wherein a polarity of a magnet fitted into the outer support member differs from a polarity of a magnet fitted into the magnet fixing hole of the inner support member.

14. The articulator according to claim 11, wherein the inner support member comprises:
 an insertion recess formed at a front side in which the shaft member is seated;
 transverse guide members disposed on upper and lower surfaces so as to guide sliding into the inner space of the outer support member;
 a screw hole formed in a side surface, wherein the lateral adjustment screw is fitted into the screw hole; and
 a magnet fixing hole which maintains a coupling force between the inner support member and the outer support member.

15. The articulator according to claim 14, wherein a polarity of a magnet fitted into the outer support member differs from a polarity of a magnet fitted into the magnet fixing hole of the inner support member.

16. The articulator according to claim 11, wherein each of the plurality of rear lower frames of the maxillary fixing part has a slot at one side, the lateral adjustment screw being fitted into the slot.

* * * * *